United States Patent [19]

Fye

[11] Patent Number: 5,031,609
[45] Date of Patent: Jul. 16, 1991

[54] POSTOPERATIVE COMPRESSION BANDAGE FOR THE HEAD

[76] Inventor: Letty A. Fye, 1025 Delphi Dr., Lafayette, Colo. 80026

[21] Appl. No.: 505,634

[22] Filed: Apr. 6, 1990

[51] Int. Cl.$^5$ .................. A61F 13/12; A61F 11/00
[52] U.S. Cl. ................... 128/163; 128/164; 128/857
[58] Field of Search ....... 128/857, 163, 164, DIG. 15, 128/155, 156, 76 R, 76 B

[56] References Cited

U.S. PATENT DOCUMENTS

| | | | |
|---|---|---|---|
| 649,896 | 5/1900 | Baughman | 128/164 |
| 862,794 | 8/1907 | Black | 128/164 |
| 1,023,358 | 4/1912 | Bender | 128/164 |
| 1,274,636 | 8/1918 | Tucker | 128/164 |
| 1,584,012 | 5/1926 | Cocroft | 128/164 |
| 1,641,471 | 9/1927 | Bliss | 128/164 |
| 1,668,794 | 5/1928 | Witherspoon | 128/14 |
| 1,693,452 | 11/1928 | McCune | 128/164 |
| 1,963,237 | 6/1934 | Knauth | 128/164 |
| 3,709,225 | 1/1973 | Sobel | 128/164 |
| 4,934,357 | 6/1990 | Frantzich | 128/164 |

Primary Examiner—Robert A. Hafer
Assistant Examiner—Michael Brown
Attorney, Agent, or Firm—Francis A. Sirr; Earl C. Hancock

[57] ABSTRACT

A post operative compression bandage for the human head is described having primary utility for use after facelift or rhytidectomy plastic surgery. The bandage includes a generally flat and unitary member that is formed of relatively thin, single ply, four-way stretch, and washable cloth-like material, preferably of about 90 percent nylon and about 10 percent lycra spandex. The unitary bandage member is formed by stitching two identically shaped cloth members at mating convex arc portions thereof, to thereby form a chin cup. Each of the two cloth members includes a neck strap, a top of the head strap, and a back of the head strap. These six straps terminate in mating hook/loop fasteners of the Velcro type. The length, width and placement of the straps are selected to achieve a desired compression of the covered head area, while at the same time minimizing the tendency of a tensioned bandage to form wrinkles, creases and the like. The bandage forms an opening about the face, thus the bandage does not interfere with chemosurgical and/or dermabrasion procedures that may have been performed upon or around the forehead, eyelids, cheeks, and/or the mouth of the patient. The portion of the bandage that covers the ears is solid, i.e. it does not contain openings. Thus, the bandage maintains the desired compression in the area of the ear, in the event that rhytidectomy procedures have been performed in that area.

14 Claims, 2 Drawing Sheets

POSTOPERATIVE COMPRESSION BANDAGE FOR THE HEAD

FIELD OF THE INVENTION

This invention relates to the field of surgery, and more particularly to a head truss, garment or bandage for use after facelift or rhytidectomy surgery.

BACKGROUND OF THE INVENTION

In the expanding field of plastic surgery there is an increasing need and demand for proper fitting, light weight, postoperative pressure garments or bandages that are comfortable, and yet provide an even distribution of compression for optimal stoppage of bleeding (i.e. hemostasis).

While the prior art teaches a variety of head appliances, these devices generally fail to meet present day plastic surgery needs for a variety of reasons, including, they are uncomfortable to wear, they are heavy devices, they do not reliably stay in place and thus tend to form wrinkles, creases and the like, and they provide for an uneven distribution of pressure to the underlying head area, and thus do not function well for optimum hemostasis.

For example, U.S. Pat. No. 3,709,225 discloses a heavy, multi layer facial contouring mask that includes a chin portion and bands that encircle the top of the head and the neck, but leaves the ear area uncovered and does not provide the required tension in the back of the head and ear area. U.S. Pat. No. 4,190,054 is similar in that it discloses a head bandage, suggested for use after surgery, having means for holding or attaching hot or cold packs, having a chin portion and a neck portion, and having an opening in the ear area.

Various prior art beauty aids provide coverage of the head, including the ear area, but these devices are of no use as a post surgery bandage. Exemplary is U.S. Pat. No. 1,963,2237 which describes a facial beauty mask of two-ply net material that covers the chin and the top of the head, and has an opening therein to leave free the central part of the face between the eye brows and the lower lip. Two ribbons are tied together behind the neck. Two other ribbons pass through an opening in the mask, and are then tied together in an area generally behind the head.

U.S. Pat. No. 1,862,588 describes a facial mask that includes an internal chin strap. Straps connected to the chin strap encircle the top of the head, while straps connected to the facial portion of the mask encircle the neck and the back of the head. U.S. Pat. Nos. 1,023,358, 1,584,012, 1,668,794, 1,678,970, 1,693,452, 1,783,080, and 2,556,793 are generally similar in that they do not leave the facial portion of the device open.

The prior art provides facial mask devices that do include an open facial area. However, these devices do not provide the critical evenly distributed pressures that are required of a bandage for use after facelift or rhytidectomy surgery. U.S. Pat. Nos. 862,794, 1,872,642, 1,996,705, 2,044,521 and 2,556,793 are examples.

Yet other prior art devices provide primarily only chin support, and are totally unsatisfactory for use after facelift surgery. U.S. Pat. Nos. 1,674,541, 2,273,964, 2,711,730, 3,572,329, 3,759,256, 4,658,811 and 4,694,823 are examples.

Thus, there remains a need for a proper fitting, light weight, adjustable, postoperative pressure bandage that is easy to apply, comfortable to wear, provides coverage for the critical head areas including the ear, the side of the jaw and under the chin, and provides an even distribution of compression for optimal stoppage of bleeding.

SUMMARY OF THE INVENTION

Figure 1:
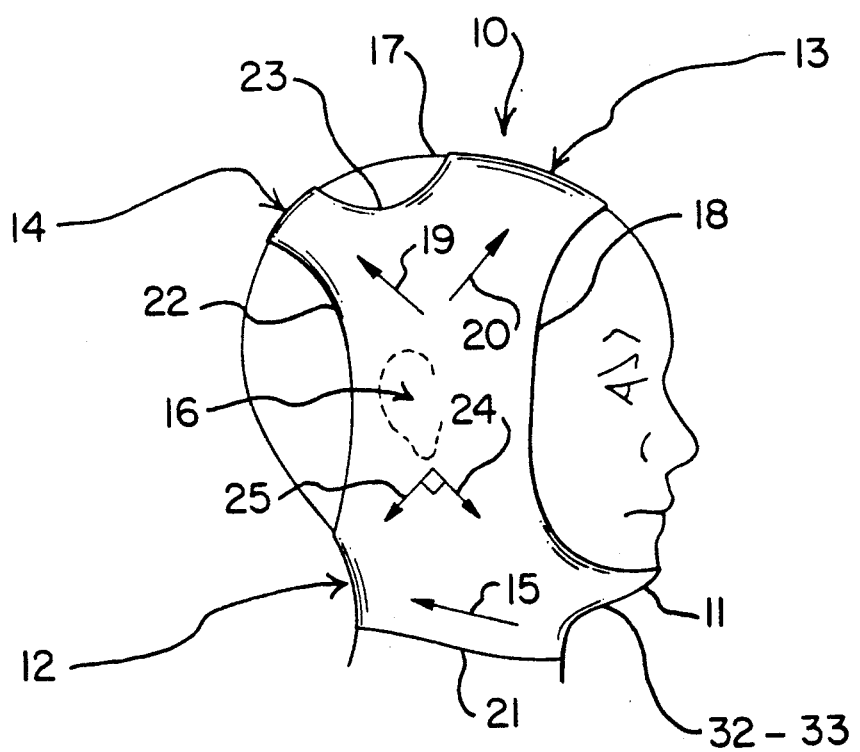
FIG. 1 is a right side view showing the bandage of the invention in place on the head of a patient.

The present invention provides a postoperative compression truss, garment or bandage for the human head having primary utility after facelift or rhytidectomy plastic surgery, including aesthetic or cosmetic surgery. The bandage of the invention reduces the swelling that usually accompanies plastic surgery under the chin, along the side of the face, and in the area of the ears. A bandage in accordance with the invention is constructed and arranged to insure a proper fit, it is light weight and it is comfortable to wear, and yet the bandage provides an even distribution of compression for optimal stoppage of bleeding.

The new and unusual light weight bandage of the invention provides even compression for optimum hemostasis. When facelift and blepharoplasty surgical procedures are combined, the bandage of the invention adds no additional stress to the blepharoplasty suture lines, and the bandage does not ride forward onto the facial area of the patient.

The bandage generally comprises a flat, unitary member that is made of a thin, single ply, four-way stretch, cloth-like material, preferably about 90 percent nylon and about 10 percent lycra spandex. This selection of material enables the bandage to be light weight and hand washable.

The single piece bandage is formed by stitching two identically shaped cloth members (one being the mirror image of the other) at mating convex arc portions thereof, to thereby form a natural chin cup. Each of the two cloth members are substantially identical in shape, and include a neck strap, a top/front of the head strap, and a top/back of the head strap. The two head straps are located on opposite sides of the head's apex, to thereby minimize shifting of the bandage on the head.

In accordance with a feature of the invention, the bandage's neck strap is proportioned to completely cover the nape (i.e. the back) of the neck. This strap does not extend appreciably upward onto the curve of the skull. In this way, a stable, firm, tube of compression bandage material covers the neck of the patient. This strap, in combination with the internal forces that are provided by the other two bandage straps, insure that there is no tendency of the bandage to wrinkle or the like in this critical neck area.

The bandage's top/back of the head strap is located above the head's ear area, where the skull begins to curve forward, and below the top apex of the skull. This strap is of generally the same width as the neck strap. The top/back of the head strap provides an internal force component that extends generally 45 degrees upward from the horizontal, and away from the bandage's facial opening. This strap functions to place the bandage in compression away from the facial area, to place the bandage in compression over the ears, and to provide a component of upward force on the bandage's neck strap area, thus minimizing shifting of the bandage on the head, and minimizing bandage folding, wrinkling and the like.

The bandage's top/front of the head strap is the widest of the three straps. This strap firmly and comfortably anchors the bandage to the front/top portion of the head, at a position that is forward of and below the apex of the skull. This strap provides an internal force component that extends generally 45 degrees upward and toward the bandage's facial opening. Thus, the top/front of the head strap provides a forward component of tension to the ear area, and provides an additional upward force to the neck/chin area.

These six straps terminate in mating hook/loop fasteners or closures of the Velcro type. Use of this type of fastener means enables the bandage to be readily adjusted for maximum comfort, consistent with maintaining adequate compression and support of the covered area. The physical proportions and the placement of the straps are selected to achieve the proper compression of the covered head area, while at the same time minimizing the tendency of the tensioned bandage to form creases, folds, and the like.

When the bandage is mounted to the head of a patient, the bandage provides an opening about the face, thus the bandage does not interfere with facial healing after chemosurgical and/or dermabrasion procedures that may have been performed upon or around the forehead, eyelids, cheeks, and/or the mouth of the patient, as a complement to a facelift procedure.

The portion of the bandage that covers the ears is solid, i.e. it does not contain openings. Thus, the bandage maintains the desired compression in the vital post-auricular suture line area. This covering of the ear is also desirable in the event that otoplasty ear surgery (i.e. a form of ear surgery designed to set disproportionately large or prominent ears closer to the head) has been performed. Otoplasty usually requires that the ears be covered with relatively bulky dressings. The light weight, four-way stretch bandage of the invention comfortably holds these post operative dressings, providing an even distribution of compression to thereby ensure adequate hemostasis.

These and other objects and advantages of the invention will be apparent to those of skill in the art upon reference to the following detailed description, which description makes reference to the drawing.

DETAILED DESCRIPTION OF THE INVENTION

This invention provides a head truss, garment or bandage for use after facelift or rhytidectomy surgery. The bandage of the invention is easy to apply to a patient's head, its straps are size adjustable, it is light weight and comfortable to wear, it provides uniform pressure to the covered head area, it holds underlying surgical dressings in place, and it maintains hemostasis.

Rhytidectomy typically is performed to remove excess, loose, and/or sagging skin from the face and/or neck. Examples are deep skin folds in the generally vertical cheek area, skin loosely hanging under the generally horizontal lower jaw (i.e. jowls), and loose skin in the generally vertical front and side of the neck.

Facelifting incisions usually start inside the hairline in the vicinity of the temples. They continue generally vertically downward, turn generally upward in an arc around the ear lob, and then extend downward at about a 45 degree angle, to terminate generally at the back of the scalp or in the nape of the neck. An incision may also extend inside the front of the ear. A small generally horizontal incision frequently is necessary under the chin to provide access to the neck skin and fat. The surgeon works through these incisions to separate the skin from the underlying fat and muscle. The skin is usually pulled up and backward in the area of the temple, and in the front and back of the ear. The excess skin is then excised. This procedure may include removing accumulations of fat from beneath the chin and neck. Sagging muscles and connective tissue may also be tightened.

A small, thin drain tube may be placed in the area of the back of the ear to allow for drainage of blood and the like. Swelling of the area is common.

When removal of pouches around the eyes, and/or eyelid surgery, is also desired, it may be done in conjunction with the rhytidectomy procedure. If such blepharoplasty is performed, the surgeon makes an incision on the upper and lower eyelids, generally into the crow's feet area at the lower edge of the eyes. Excess skin and fat is then removed.

The bandage of the invention maintains relatively uniform compression force against the entire surface of the chin, particularly including the underside of the chin, the side of a patient's head, the sides of the chin, and both in front of and behind the ears. The bandage is placed on the patient's head by first securing the neck strap. Then the top/front head strap is fastened, and lastly the top/back head strap is fastened.

In FIG. 1 the bandage 10 of the invention is shown secured to the head of a patient. Bandage 10 comprises a generally flat, unitary, single thickness, hand washable, member that is made of a four-way stretch cloth-like material, preferably of about 90 percent nylon and about 10 percent lycra spandex.

As will be explained, bandage 10 is formed by stitching two identically shaped cloth members at mating convex arc portions thereof, to thereby form a natural chin cup 11. The use of a flat-felled seam is preferred. Cup 11 secures the bandage to the front vertical portion of the patient's jaw, as shown. Each of the two cloth members are substantially identical in shape, and include a neck strap 12, a top/front of the head strap 13, and a top/back of the head strap 14.

The bandage's neck strap 12 is proportioned to completely cover the nape of the patient's neck. Strap 12 does not extend appreciably upward onto the curve of the skull. Neck strap 12 is about 2 ½ inches wide, and provides a generally horizontal force component within bandage 10, as is exemplified by arrow 15.

The bandage's top/back of the head strap 14 is located above the patient's ear area 16, where the skull begins to curve forward, and below the top apex 17 of the skull. Strap 14 is of generally the same width as neck strap 12, i.e. about 2 ½ inches wide. Strap 14 operates to provide a force component within bandage 10 that extends generally 45 degrees upward from the horizontal, and away from the bandage's oval shaped facial opening 18. This force component is exemplified by arrow 19. The major axis of facial opening 18 extends generally vertical. Strap 14 operates to place bandage 10 in compression away from facial area 18, operates to place the bandage in compression over ear area 16, and internal force component 19 provides a vertically upward force component to the bandage's neck strap area, thus minimizing shifting of bandage 10 on the patient's head, and minimizing folding, wrinkling, and the like of bandage 10.

The bandage's top/front of the head strap 13 is the widest of the three straps, being about 3 ¾ inches wide. Strap 13 firmly and comfortable anchors bandage 10 to the front/top portion of the skull, at a position below its apex 17. Strap 13 provides an internal force component 20 that extends generally 45 degrees upward and toward facial opening 18. The internal force component 20 that is provided by strap 13 can be resolved into a forward and generally horizontal component of tension to ear area 16, and into an additional upward component of tension to the patient's neck/chin area.

Once bandage 10 is in place on the head of the patient, as is shown in FIG. 1, a pair of guadrature related force vectors 24,25 operate in the area of the patient's upper jaw, thus holding chin cup 11 firmly in place, and holding bandage 10 firmly in place over the patient's ear area 16.

The six straps making up straps 12–14 of FIG. 1 terminate at a location that is in the plane of FIG. 1 and in mating hook/loop fasteners or closures of the well known Velcro type. These hook/loop fastening portions are of substantially identical dimension, and are as wide as the corresponding straps 12–14. The length of these hook/loop portions are about 1 ¾ inch. Use of this type of fastener means enables bandage 10 to be readily adjusted to an individual patient for maximum comfort, consistent with maintaining adequate compression and support of the covered area of the patient's chin, side of the face and ear areas. An exemplary adjustment range of about 1 ¼ inch exists for hook and loop portions that are each about 1 ¾ inch long.

The above dimensions are to be considered as only typical dimensions, since within the spirit and scope of the invention the physical proportions and the placement of straps 12–14 may be selected to achieve the proper compression of the covered head area, while at the same time minimizing the tendency of the tensioned bandage to form creases, folds, and the like. In fact, it may be desirable to produce bandages 10 of somewhat different dimensions to better suit men, women and children.

When bandage 10 is mounted to the head of a patient, the bandage provides an opening 18 about the face, thus bandage 10 does not interfere with facial healing after chemosurgical and/or dermabrasion procedures that may have been performed upon or around the forehead, eyelids, cheeks, and/or the mouth.

The portion of four-way stretch bandage 10 that covers ear area 16 is solid. Thus, bandage 10 maintains the desired compression in the vital post-auricular suture line area. This covering of ear area 16 is also desirable in the event that otoplasty ear surgery has been performed.

The light weight of bandage 10 comfortably holds post operative dressings in place, provides an even distribution of compression, and providing adequate hemostasis.

Bandage 10 includes four openings, namely (1) a neck opening that is defined by edge 21, (2) a back of the head opening that is defined by edge 22, (3) a top of the head opening that is defined by edge 23, and a facial opening that is defined by edge 18. All of these bandage edges are finished, for example by the use of a zig-zag stitch. Note that all of these bandage edges provide smooth curved lines, rather than having corners that are formed by the joining of relatively straight lines. Importantly, this construction and arrangement aids in providing uniform tension within the body of bandage 10.

Figure 2:
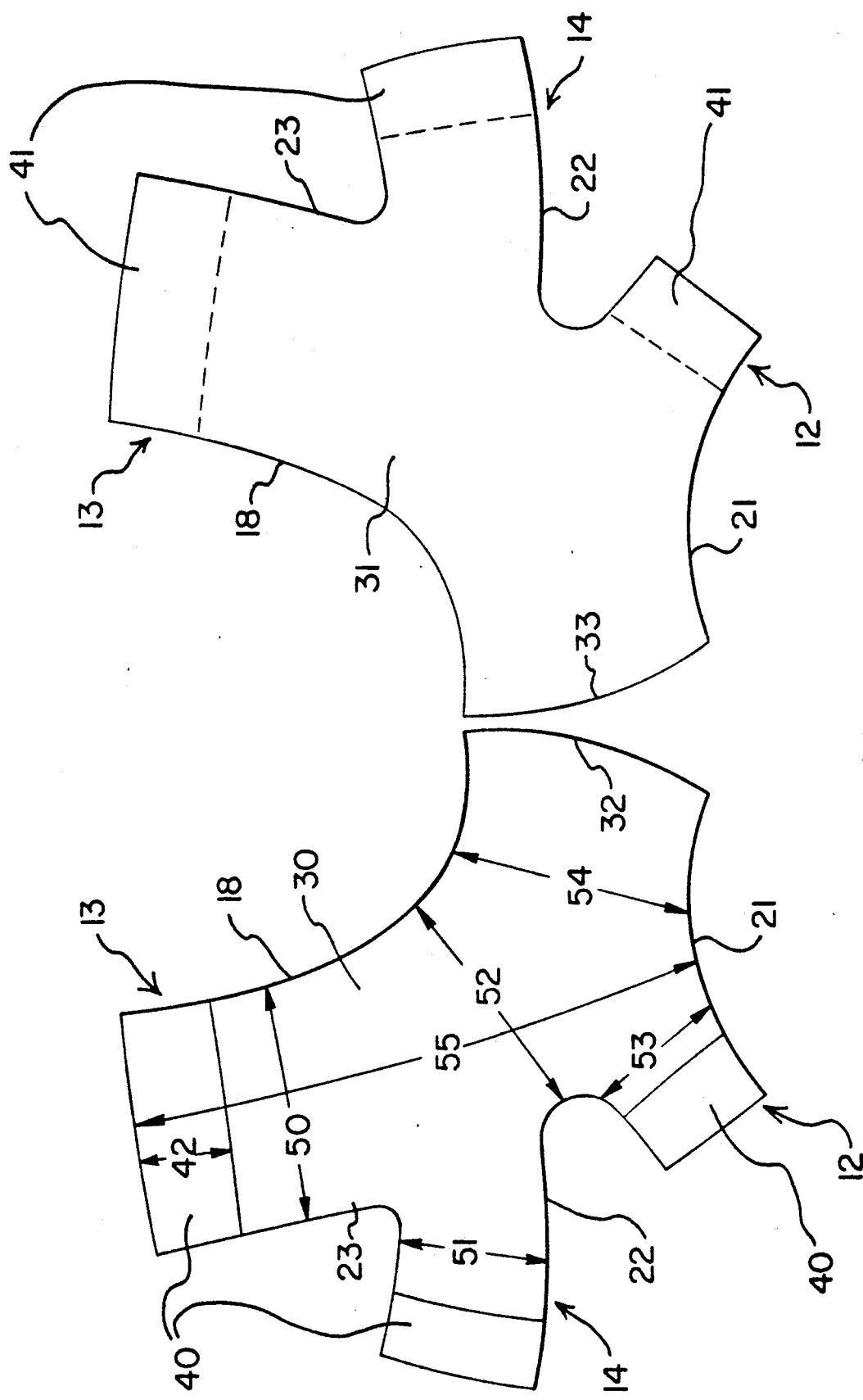
FIG. 2 is an inside plan view of the bandage of FIG. 1 prior to the two portions thereof being joined together to form the chin cup that is shown in FIG. 1.

FIG. 2 is an inside plan view (i.e. a view of the side of the bandage that is placed adjacent to the patient's head) of bandage 10 prior to the left side portion 30 and the right side portion 31 thereof being joined together at mating convex arc edges 32 and 33. The use of arc shaped edges 32–33 insures that after these edges are stitched together, a naturally shaped chin cup 11 is formed, as is shown in FIG. 1. The seam that is formed as edges 32–33 are joined should be a seam that is smooth on the side of the bandage that engages a patient's head, so as not to unduly stress the associated area of the chin and the neck. A flat felled seam is preferred.

Note that bandage portions 30 and 31 are of an identical shape, one portion being the mirror image of the other portion.

The bandage's three strap portions 12, 13 and 14, and the bandage's four edge portions 18, 21, 22 and 23, all of which are described above in relation to FIG. 1, retain the same numbers in FIG. 2. FIG. 2 also shows the location of hook fastener portions 40 that mate with loop fastener portions 41. These mating hook/loop fasteners enable straps 12–14 to be secured to the head of a patient, as is shown in FIG. 1. In FIG. 2 the three hook portions 40 are exposed to view, whereas the three loop portions 41 are located on the underside of bandage portion 31 in this figure.

When the bandage is placed on the head of a patient, the Velcro type hook/loop fasteners 40–41 are brought into physical engagement, and the bandage straps are thus secured, as shown in FIG. 1. As stated previously, the width dimensions of hook/loop fasteners 40–41 approximate the width of the associated straps. The length dimension (see dimension 42) of hook/loop fasteners 40–41 of all substantially equal, for example about 1 ½ inch, thus providing a range of length adjustment for straps 12–14.

While the specific dimensions of bandage 10 are not to be considered as a limitation on the invention, an exemplary set of unstretched dimensions for each of the two bandage portions 30–31 is as follows: dimension 50, about 3 ½ inch; dimension 51, about 2 ¼ inch; dimension 52, about 4 ¾ inch; dimension 53, about 2 ¾ inch; dimension 54, about 4 ¾ inch; and dimension 55, about 10 ¼ inch. As will be appreciated by those of skill in the art, these specific dimensions may best suit an average size female individual. Bandages within the spirit and scope of this invention can be made for other individuals, for example an average size child or an average size male, merely by scaling up or down the size of the bandage, using generally the same dimension ratio.

As is apparent from the above description of preferred embodiments of the invention, the invention provides a postoperative compression bandage for the human head having utility after plastic surgery, the bandage being uniquely constructed and arranged to insure a proper fit, to be light weight and comfortable to wear, and yet the bandage provides an even distribution of compression for optimal stoppage of bleeding.

Since those skilled in the art will, upon learning of the present invention, visualize yet other embodiments thereof that are within the spirit and scope of the invention, it is intended that the present invention be limited only by the following claims.

What is claimed is:

1. A postoperative compression bandage for use in association with a human patient's head after plastic surgery has been performed in the neck, chin, cheek and/or ear area of the head, the bandage comprising;
   a generally flat, unitary member made of a thin four-way stretch cloth-like material, said unitary member being formed by stitching two mirror shaped cloth-like members together at mating convex arc portions thereof, to thereby form a seam that is arranged to extend vertically down the center of the chin and front neck of the patient, and thus to form a convex shaped chin cup that is arranged to receive the chin area of the patient,
   each of said cloth members include a mating neck strap portion, a mating top/front of the head strap portion, and a mating top/back of the head strap portion,
   said head strap portions being arranged for positioning on opposite sides of a patient's head apex, to thereby minimize shifting of the bandage on the head,
   said neck strap portions being arranged to cover the nape of the neck so as not to extend appreciably upward onto the curve of the patient's head, thus providing a tube of bandage compression covering the patient's neck and chin area,
   said strap portions, when said bandage is secured to a patient's head, functioning to provide forces internal of said bandage that operate to reduce the tendency of a compression bandage to wrinkle and the like, and
   the portion of said cloth members located so as to cover the ear area of the patient being free of openings.

2. The bandage of claim 1 wherein said top/back of the head strap portion is arranged to be located above the patient's ear area and below the patient's head apex.

3. The bandage of claim 2 wherein said top/front of the head strap is arranged to be located on the facial side of the patient's head apex.

4. The bandage of claim 3 including adjustable fastening means associated with said strap portions.

5. The bandage of claim 4 wherein said adjustable fastening means comprise mating hook/loop fastener means.

6. The bandage of claim 5 wherein said seam is smooth on the side of said bandage that is arranged to be adjacent to the head.

7. The bandage of claim 6 wherein said seam is a flat-felled seam.

8. The bandage of claim 6 wherein the external edges of said bandage comprise smooth curving lines, so as to minimize the creation of unequal tension within said bandage.

9. The bandage of claim 1 wherein said unitary member comprises a light weight, single ply material of about 90 percent nylon and about 10 percent lycra operable to provide an even distribution of compression to a patient's head for optimal stoppage of bleeding.

10. The bandage of claim 9 wherein said strap portions terminate in adjustable hook/loop fastening means.

11. The bandage of claim 10 wherein said bandage provides an facial opening to accommodate a patient's face in an unobstructed manner, so as not to interfere with facial healing after chemosurgical and/or dermabrasion procedures that may have been performed upon the patient as a complement to plastic surgery.

12. The bandage of claim 11 wherein said top/back of the head strap portion is arranged to provide an internal bandage force component that extends generally 45 degrees upward from the horizontal, and away from said facial opening, to thereby place said bandage in compression away from the facial area, to place said bandage in compression over the ear area, and to provide a component of upward force on the neck strap portion of said bandage, thus minimizing bandage shifting, folding, wrinkling and the like.

13. The bandage of claim 12 wherein said front/back of the head strap portion operates to anchor said bandage to the front/top portion of a patient's head at a position that is forward of and below the apex of the patient's head, said front/back of the head strap portion operating to provide an internal bandage force component the extends generally 45 degrees upward and toward said facial opening, to place said bandage in compression over the ear area, and to provide a component of upward force on the neck strap portion of said bandage.

14. The bandage of claim 13 wherein strap portions operate to provide a pair of quadrature related internal bandage forces that extend generally 45 degrees downward, to place said bandage in compression over the ear area and the chin area, and to provide a component of upward force on the neck strap portion of said bandage.

* * * * *